(12) United States Patent
Ditrich

(10) Patent No.: US 7,968,328 B2
(45) Date of Patent: Jun. 28, 2011

(54) METHOD FOR PRODUCING OPTICALLY ACTIVE AMINOALKYLPHENOLS

(75) Inventor: Klaus Ditrich, Goennheim (DE)

(73) Assignee: BASF SE, Ludwigshafen (DE)

( * ) Notice: Subject to any disclaimer, the term of this patent is extended or adjusted under 35 U.S.C. 154(b) by 817 days.

(21) Appl. No.: 11/917,987

(22) PCT Filed: Jun. 19, 2006

(86) PCT No.: PCT/EP2006/063314
§ 371 (c)(1),
(2), (4) Date: Dec. 18, 2007

(87) PCT Pub. No.: WO2006/136538
PCT Pub. Date: Dec. 28, 2006

(65) Prior Publication Data
US 2010/0209980 A1    Aug. 19, 2010

(30) Foreign Application Priority Data
Jun. 20, 2005   (DE) .......................... 10 2005 028 492

(51) Int. Cl.
*C12P 13/00*   (2006.01)
*C12P 41/00*   (2006.01)
(52) U.S. Cl. ....................................... 435/280; 435/128
(58) Field of Classification Search .................. None
See application file for complete search history.

(56) References Cited

U.S. PATENT DOCUMENTS

| 4,904,680 A | 2/1990 | Matsui et al. |
| 5,728,876 A | 3/1998 | Balkenhohl et al. |
| 5,965,032 A | 10/1999 | Frede et al. |
| 6,068,996 A * | 5/2000 | Dreisbach et al. ............ 435/128 |
| 6,214,608 B1 | 4/2001 | Balkenhohl et al. |
| 6,387,692 B1 | 5/2002 | Stelzer et al. |
| 6,576,795 B1 | 6/2003 | Funke et al. |

FOREIGN PATENT DOCUMENTS

| DE | 19603575 A1 | 8/1997 |
| EP | 0311385 A2 | 4/1989 |
| JP | 2000238 A | 1/1990 |
| JP | 10512759 T | 12/1998 |
| WO | WO-95/08636 A1 | 3/1995 |
| WO | WO-96/23894 A1 | 8/1996 |
| WO | WO-97/20946 A1 | 6/1997 |

OTHER PUBLICATIONS

Breuer et al., "Industrial Methods for the Production of Optically Active Intermediates", *Angew. Chem. Int. Ed.*, vol. 43, pp. 788-824 (2004).

Kündig, E. P., et al., "Asymmetric Synthesis of 2-(1-Aminoethyl)phenols", Helvetica Chimica Acta, 2004, vol. 87, No. 3, pp. 561-579.

* cited by examiner

*Primary Examiner* — Sandra E Saucier
(74) *Attorney, Agent, or Firm* — Connolly Bove Lodge & Hutz LLP

(57) ABSTRACT

The invention relates to a method for the enantioselective N-acylation of aminoalkylphenols, and to a method for producing enantiomer-pure compounds of formulae (I-S) and/or (I-R).

10 Claims, No Drawings

METHOD FOR PRODUCING OPTICALLY ACTIVE AMINOALKYLPHENOLS

RELATED APPLICATIONS

This application is a national stage application (under 35 U.S.C. §371) of PCT/EP2006/063314, filed Jun. 19, 2006, which claims benefit of German application 10 2005 028 492.2, filed Jun. 20, 2005.

The present invention relates to a process for enantioselectively N-acylating aminoalkylphenols and to a process for preparing enantiomerically pure compounds of the formulae (I-S) and/or (I-R)

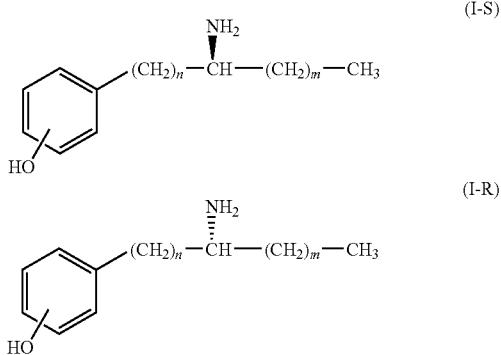

The preparation of enantiomerically pure aminoalkylbenzenes by optical resolution is known. For instance, WO 95/08636 describes a process for optically resolving primary and secondary amines by reacting them with an ester in the presence of a hydrolase and then separating the one enantioselectively acylated amine from the unacylated antipode. An optical resolution of alkylaminohydroxybenzenes, in contrast, is not described.

U.S. Pat. No. 4,904,680 describes a process for optically resolving 4-(1-aminoethyl)phenol by reacting the enantiomer mixture with malic acid. However, the reaction proceeds with poor yields, and the optical purity is still not satisfactory either.

It was an object of the present invention to provide an efficient process for preparing essentially enantiomerically pure compounds of the formulae (I-S) and/or (I-R).

It has now been found that, surprisingly, amines (I-S) and/or (I-R) can be obtained when the enantiomer mixture, especially the racemate of these amines, is acylated enantioselectively in the presence of a hydrolase. It is a prerequisite that the hydroxyl function on the benzene ring is protected before the acylation.

The invention therefore relates to a process for enantioselectively acylating aminoalkylphenols (process A), in which an enantiomer mixture of the formula (II)

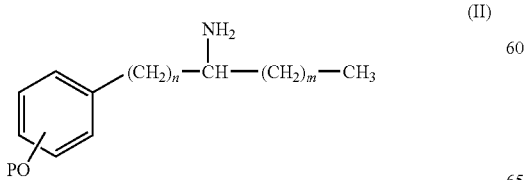

in which

P is a protecting group,
n is 0, 1 or 2 and
m is 0, 1 or 2
is reacted with an acylating agent in the presence of a hydrolase to obtain a mixture in which one enantiomer is present essentially in the acylated form and the other enantiomer is present essentially in the unacylated form.

The invention further provides a process (process B) for preparing essentially enantiomerically pure compounds of the formulae (I-S) and/or (I-R)

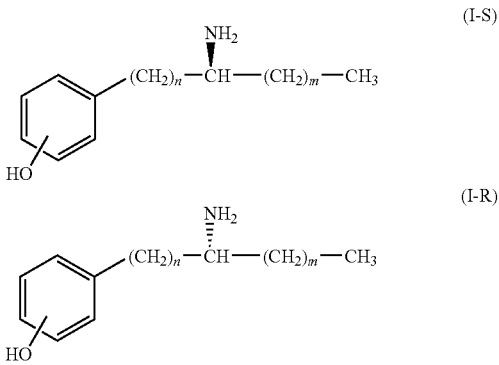

in which
n is 0, 1 or 2 and
m is 0, 1 or 2,
comprising the following steps:
(i) reacting an enantiomer mixture of the formula (II)

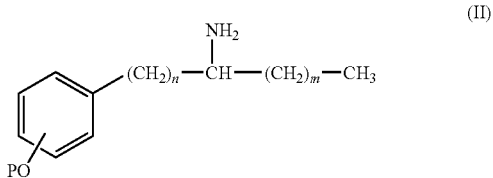

in which
P is a protecting group, and
m and n are each as defined above,
with an acylating agent in the presence of a hydrolase to obtain a mixture in which one enantiomer is present essentially in acylated form and the other enantiomer is present essentially in the unacylated form;
(ii) removing the unacylated enantiomer of compound (II) from the mixture obtained in step (i);
(iii) deprotecting the unacylated enantiomer of compound (II) obtained in step (ii) to give the amine (I-S) or (I-R); and
(iv) if desired hydrolyzing the essentially acylated enantiomer of compound (II) obtained in step (i) to give the corresponding unacylated enantiomer of the amine (II) and subsequently deprotecting it to give the amine (I-R) or (I-S).

The remarks made below regarding preferred embodiments of the process according to the invention, of the reactants and of the products apply both taken alone and especially in combination with one another.

Essentially enantiomerically pure compounds of the formulae (I-S) and (I-R) should be understood in the context of the present invention to mean that they are present in an enantiomeric purity of in each case at least 95% ee, preferably at least 96% ee and in particular at least 97% ee.

In process A or in step (i) of process B, preference is given to obtaining a mixture in which the S enantiomer is present essentially in unacylated form and the R enantiomer is present in essentially acylated form.

"Essentially unacylated enantiomer of the compound (II)" shall be understood to mean that at least 95%, preferably at least 97%, in particular at least 98%, of this enantiomer of the compound (II) is not acylated. The expression "essentially acylated enantiomer of the compound (II)" means correspondingly that at least 95%, preferably at least 97%, more preferably at least 98%, of this enantiomer of compound (II) is present in acylated form.

"Essentially unacylated S enantiomer of compound (II)" shall correspondingly be understood to mean that at least 95%, preferably at least 97%, in particular at least 98%, of the S enantiomer of the compound (II) is not acylated. The expression "essentially acylated R enantiomer of compound (II)" means correspondingly that at least 95%, preferably at least 97%, more preferably at least 98%, of the R enantiomer of compound (II) is present in acylated form.

The hydrolyse used in process A or in step (i) of process B is preferably a protease and especially a lipase. This brings about a selective N-acylation (amidation) of only one of the two enantiomers of compound (II). It preferably brings about the selective amidation of the R enantiomer of compound (II). The hydrolase is preferably obtained from a microorganism, more preferably from a bacterium or a yeast. Likewise suitable are hydrolases which are obtainable by recombinant processes. The hydrolase can be used in purified or partly purified form or in the form of the microorganism itself. Processes for obtaining and purifying hydrolases from microorganisms are sufficiently well known to those skilled in the art, for example from EP-A-11149849 or EP-A-1069183. Preference is given to using the hydrolase in purified form.

The hydrolase may be used in free (i.e. in native form) or immobilized form. An immobilized enzyme is understood to mean an enzyme which is fixed to an inert support. Suitable support materials and the enzymes immobilized thereto are known from EP-A-1149849, EP-A-1 069 183 and DE-A 100193773 and from the literature references cited therein. In this context, reference is made to the full disclosure of these documents. The suitable support materials include, for example, clays, clay minerals such as kaolinite, diatomaceous earth, perlite, silicon dioxide, aluminum oxide, sodium carbonate, calcium carbonate, cellulose powder, anion exchange materials, synthetic polymers such as polystyrene, acrylic resins, phenol-formaldehyde resins, polyurethanes and polyolefins such as polyethylene and polypropylene. To prepare the supported enzymes, the support materials are typically used in a finely divided, particulate form, preference being given to porous forms. The particle size of the support material is typically not more than 5 mm, in particular not more than 2 mm (sieve grade).

Preference is given to using lipases (triacylglycerolacylhydrolases; EC 3.1.1.3). Among these, preference is given to lipases which are obtained from bacteria of the *Burkholderia* or *Pseudomonas* genera or from yeasts of the *Candida* genus.

Examples of *Burkholderia* species are *Burkholderia ambifaria* (e.g. strains ATCC BAA-244, CCUG 44356, LMG 19182); *Burkholderia andropogonis* (e.g. strains ATCC 23061, CCUG 32772, CFBP 2421, CIP 105771, DSM 9511, ICMP 2807, JCM 10487, LMG 2129, NCPPB 934, NRRL B-14296); *Burkholderia calcdonica* (e.g. strains W50D, CCUG 42236, CIP 107098, LMG 19076); *Burkholderia caribensis* (e.g. strains MWAP 64, CCUG 42847, CIP 106784, DSM 13236, LMG 18531); *Burkholderia caryophylli* (e.g. strains ATCC 25418, CCUG 20834, CFBP 2429, CFBP 3818, CIP 105770, DSM 50341, HAMBI 2159, ICMP 512, JCM 9310, JCM 10488, LMG 2155, NCPPB 2151); *Burkholderia cepacia* (e.g. strains Ballard 717, 717-ICPB 25, ATCC 25416, CCUG 12691, CCUG 13226, CFBP 2227, CIP 80.24, DSM 7288, HAMBI 1976, ICMP 5796, IFO 14074, JCM 5964, LMG 1222, NCCB 76047, NCPPB 2993, NCTC 10743, NRRL B-14810); *Burkholderia cocovenenans* (e.g. strains ATCC 33664, CFBP 4790, DSM 11318, JCM 10561, LMG 11626, NCIMB 9450); *Burkholderia fungorum* (e.g. strains Croize P763-2, CCUG 31961, CIP 107096, LMG 16225); *Burkholderia gladioli* (e.g. strains ATCC 10248, CCUG 1782, CFBP 2427, CIP 105410, DSM 4285, HAMBI 2157, ICMP 3950, IFO 13700, JCM 9311, LMG 2216, NCCB 38018, NCPPB 1891, NCTC 12378, NRRL B-793); *Burkholderia glathei* (e.g. strains ATCC 29195, CFBP 4791, CIP 105421, DSM 50014, JCM 10563, LMG 14190); *Burkholderia glumae* (e.g. strains ATCC 33617, CCUG 20835, CFBP 4900, CFBP 2430, CIP 106418, DSM 9512, ICMP 3655, LMG 2196, NCPPB 2981, NIAES 1169); *Burkholderia graminis* (e.g. strains C4D1M, ATCC 700544, CCUG 42231, CIP 106649, LMG 18924); *Burkholderia kururiensis* (e.g. strains KP 23, ATCC 700977, CIP 106643, DSM 13646, JCM 10599, LMG 19447); *Burkholderia mallei* (e.g. strains ATCC 23344, NCTC 12938); *Burkholderia multivorans* (e.g. strains ATCC BAA-247, CCUG 34080, CIP 105495, DSM 13243, LMG 13010, NCTC 13007); *Burkholderia norimbergensis* (e.g. strains R2, ATCC BAA-65, CCUG 39188, CFBP 4792, DSM 11628, CIP 105463, JCM 10565, LMG 18379); *Burkholderia phenazinium* (e.g. strains ATCC 33666, CCUG 20836, CFBP 4793, CIP 106502, DSM 10684, JCM 10564, LMG 2247, NCIB 11027); *Burkholderia pikettii* (e.g. strains ATCC 27511, CCUG 3318, CFBP 2459, CIP 73.23, DSM 6297, HAMBI 2158, JCM 5969, LMG 5942, NCTC 11149); *Burkholderia plantarii* (e.g. strains AZ 8201, ATCC 43733, CCUG 23368, CFBP 3573, CFBP 3997, CIP 105769, DSM 9509, ICMP 9424, JCM 5492, LMG 9035, NCPPB 3590, NIAES 1723); *Burkholderia pseudomallei* (e.g. strains WRAIR 286, ATCC 23343, NCTC 12939); *Burkholderia pyrrocinia* (e.g. strains ATCC 15958, CFBP 4794, CIP 105874, DSM 10685, LMG 14191); *Burkholderia sacchari* (e.g. strains CCT 6771, CIP 107211, IPT 101, LMG 19450); *Burkholderia solanacearum* (e.g. strains A. Kelman 60-1, ATCC 11696, CCUG 14272, CFBP 2047, CIP 104762, DSM 9544, ICMP 5712, JCM 10489, LMG 2299, NCAIM B.01459, NCPPB 325, NRRL B-3212); *Burkholderia stabilis* (e.g. strains ATCC BAA-67, CCUG 34168, CIP 106845, LMG 14294, NCTC 13011); *Burkholderia thailandensis* (e.g. strains E 264, ATCC 700388, CIP 106301, DSM 13276); *Burkholderia ubonensis* (e.g. strains EY 3383, CIP 107078, NCTC 13147); *Burkholderia vandii* (e.g. strains VA-1316, ATCC 51545, CFBP 4795, DSM 9510, JCM 7957, LMG 16020); *Burkholderia vietnamiensis* (e.g. strains TVV 75, ATCC BAA-248, CCUG 34169, CFBP 4796, CIP 105875, DSM 11319, JCM 10562, LMG 10929).

Examples of *Pseudomonas* species are *Pseudomonas aeruginosa* (e.g. strains ATCC 10145, DSM 50071), *Pseudomonas agarici* (e.g. strains ATCC 25941, DSM 11810), *Pseudomonas alcaligenes* (e.g. strains ATCC 14909, DSM 50342), *Pseudomonas amygdali* (e.g. strains ATCC 337614, DSM 7298), *Pseudomonas anguiliseptica* (e.g. strains ATCC 33660, DSM 12111), *Pseudomonas antimicrobica* (e.g. strains DSM 8361, NCIB 9898, LMG 18920), *Pseudomonas aspleni* (e.g. strains ATCC 23835, CCUG 32773), *Pseudomonas aurantiaca* (e.g. strains ATCC 33663, CIP 106710), *Pseudomonas aureofaciens* (e.g. strains ATCC 13985, CFBP 2133), *Pseudomonas avellanae* (e.g. strains DSM 11809, NCPPB 3487), *Pseudomonas azotoformans* (e.g. strains CIP 106744, JCM 7733), *Pseudomonas balearica* (e.g. strains DSM 6083, CIP 105297), *Pseudomonas beijerinsckii* (e.g. strains ATCC 19372, DSM 6083), *Pseudomonas beteli* (e.g. strains ATCC 19861, CFBP 4337), *Pseudomonas boreopolis* (e.g. strains ATCC 33662, CIP 106717), *Pseudomonas carboxyhydrogena* (e.g. strains ATCC 29978, DSM 1083), *Pseudomonas caricapapayae* (e.g. strains ATCC 33615, CCUG 32775), *Pseudomonas cichorii* (e.g. strains ATCC 10857, DSM 50259), *Pseudomonas cissicola* (e.g. strains ATCC 33616, CCUG 18839), *Pseudomonas citronellolis* (e.g. strains ATCC 13674, DSM 50332), *Pseudomonas coronafaciens* (e.g. strains DSM 50261, DSM 50262), *Pseudomonas corrugata* (e.g. strains ATCC 29736, DSM 7228), *Pseudomonas doudoroffii* (e.g. strains ATCC 27123, DSM 7028), *Pseudomonas echinoides* (e.g. strains ATCC 14820, DSM 1805), *Pseudomonas elongata* (e.g. strains ATCC 10144, DSM 6810), *Pseudomonas ficuserectae* (e.g. strains ATCC 35104, CCUG 32779), *Pseudomonas flavescens* (e.g. strains ATCC 51555, DSM 12071), *Pseudomonas flectens* (e.g. strains ATCC 12775, CFBB 3281), *Pseudomonas fluorescens* (e.g. strains ATCC 13525, DSM 50090), *Pseudomonas fragi* (e.g. strains ATCC 4973, DSM 3456), *Pseudomonas fulva* (e.g. strains ATCC 31418, CIP 106765), *Pseudomonas fuscovaginae* (e.g. strains CCUG 32780, DSM 7231), *Pseudomonas gelidicola* (e.g. strains CIP 106748), *Pseudomonas geniculata* (e.g. strains ATCC 19374, LMG 2195), *Pseudomonas glathei* (e.g. strains ATCC 29195, DSM 50014), *Pseudomonas halophile* (e.g. strains ATCC 49241, DSM 3050), *Pseudomonas hibiscicola* (e.g. strains ATCC 19867, LMG 980), *Pseudomonas huttiensis* (e.g. strains ATCC 14670, DSM 10281), *Pseudomonas iners* (e.g. strain CIP 106746), *Pseudomonas lancelota* (e.g. strains ATCC 14669, CFBP 5587), *Pseudomonas lemoignei* (e.g. strains ATCC 17989, DSM 7445), *Pseudomonas lundensis* (e.g. strains ATCC 19968, DSM 6252), *Pseudomonas luteola* (e.g. strains ATCC 43273, DSM 6975), *Pseudomonas marginalis* (e.g. strains ATCC 10844, DSM 13124), *Pseudomonas meliae* (e.g. strains ATCC 33050, DSM 6759), *Pseudomonas mendocina* (e.g. strains ATCC 25411, DSM 50017), *Pseudomonas mucidolens* (e.g. strains ATCC 4685, CCUG 1424), *Pseudomonas monteilli* (e.g. strains ATCC 700476, DSM 14164), *Pseudomonas nautica* (e.g. strains ATCC 27132, DSM 50418), *Pseudomonas nitroreducens* (e.g. strains ATCC 33634, DSM 14399), *Pseudomonas oleovorans* (e.g. strains ATCC 8062, DSM 1045), *Pseudomonas oryzihabitans* (e.g. strains ATCC 43272, DSM 6835), *Pseudomonas pertucinogena* (e.g. strains ATCC 190, CCUG 7832), *Pseudomonas phenazinium* (e.g. strains ATCC 33666, DSM 10684), *Pseudomonas pictorum* (e.g. strains ATCC 23328, LMG 981), *Pseudomonas pseudoalcaligenes* (e.g. strains ATCC 17440, DSM 50188), *Pseudomonas putida* (e.g. strains ATCC 12633, DSM 291), *Pseudomonas pyrrocinia* (e.g. strains ATCC 15958, DSM 10685), *Pseudomonas resinovorans* (e.g. strains ATCC 14235, CCUG 2473), *Pseudomonas rhodesiae* (e.g. strains CCUG 38732, DSM 14020), *Pseudomonas saccharophila* (e.g. strains ATCC 15946, DSM 654), *Pseudomonas savastanoi* (e.g. strains ATCC 13522, CFBP 1670), *Pseudomonas spinosa* (e.g. strain ATCC 14606), *Pseudomonas stanieri* (e.g. strains ATCC 27130, DSM 7027), *Pseudomonas straminae* (e.g. strains ATCC 33636, CIP 106745), *Pseudomonas stutzeri* (e.g. strains ATCC 17588, DSM 5190), *Pseudomonas synxantha* (e.g. strains ATCC 9890, CFBP 5591), *Pseudomonas syringae* (e.g. strains ATCC 19310, DSM 6693), *Pseudomonas syzygii* (e.g. strains ATCC 49543, DSM 7385), *Pseudomonas taetrolens* (e.g. strains ATCC 4683, CFBP 5592), *Pseudomonas tolaasii* (e.g. strains ATCC 33618, CCUG 32782), *Pseudomonas veronii* (e.g. strains ATCC 700272, DSM 11331), *Pseudomonas viridiflava* (e.g. strains ATCC 13223, DSM 11124), *Pseudomonas vulgaris, Pseudomonas wisconsinensis* and *Pseudomonas* spec. DSM 8246. Among these, preference is given to lipases from *Burkholderia glumae, Burkholderia plantarii, Burkholderia cepacia, Pseudomonas aeruginosa, Pseudomonas fluorescens, Pseudomonas fragi, Pseudomonas luteola, Pseudomonas vulgaris, Pseudomonas wisconsinensis* and *Pseudomonas* spec. DSM 8246. Particular preference is given to lipases from *Pseudomonas* spec. DSM 8246.

Examples of *Candida* species are *Candida albomarginata* (e.g. strain DSM 70015), *Candida antarctica* (e.g. strain DSM 70725), *Candida bacarum* (e.g. strain DSM 70854), *Candida bogoriensis* (e.g. strain DSM 70872), *Candida boidinii* (e.g. strains DSM 70026, 70024, 70033, 70034), *Candida bovina* (e.g. strain DSM 70156), *Candida brumptii* (e.g. strain DSM 70040), *Candida cacaoi* (e.g. strain DSM 2226), *Candida cariosilignicola* (e.g. strain DSM 2148), *Candida chalmersii* (e.g. strain DSM 70126), *Candida ciferii* (e.g. strain DSM 70749), *Candida cylindracea* (e.g. strain DSM 2031), *Candida ernobii* (e.g. strain DSM 70858), *Candida famata* (e.g. strain DSM 70590), *Candida freyschussii* (e.g. strain DSM 70047), *Candida friederichii* (e.g. strain DSM 70050), *Candida glabrata* (e.g. strains DSM 6425, 11226, 70614, 70615), *Candida guillermondi* (e.g. strains DSM 11947, 70051, 70052), *Candida haemulonii* (e.g. strain DSM 70624), *Candida inconspicua* (e.g. strain DSM 70631), *Candida ingens* (e.g. strains DSM 70068, 70069), *Candida intermedia* (e.g. strain DSM 70753), *Candida kefyr* (e.g. strains DSM 70073, 70106), *Candida krusei* (e.g. strains DSM 6128, 11956, 70075, 70079, 70086), *Candida lactiscondensi* (e.g. strain DSM 70635), *Candida lambica* (e.g. strains DSM 70090, 70095), *Candida lipolytica* (e.g. strains DSM 1345, 3286, 8218, 70561 or 70562), *Candida lusitaniae* (e.g. strain DSM 70102), *Candida macedoniensis* (e.g. strain DSM 70106), *Candida magnoliae* (e.g. strains DSM 70638, 70639), *Candida membranaefaciens* (e.g. strain DSM 70109), *Candida multigemnis* (e.g. strain DSM 70862), *Candida mycoderma* (e.g. strain DSM 70184), *Candida nemodendra* (e.g. strain DSM 70647), *Candida nitratophila* (e.g. strain DSM 70649), *Candida norvegica* (e.g. strain DSM 70862), *Candida parapsilosis* (e.g. strains DSM 5784, 4237, 11224, 70125, 70126), *Candida pelliculosa* (e.g. strain DSM 70130), *Candida pini* (e.g. strain DSM 70653), *Candida pulcherrima* (e.g. strain DSM 70336), *Candida punicea* (e.g. strain DSM 4657), *Candida pustula* (e.g. strain DSM 70865), *Candida rugosa* (e.g. strain DSM 70761), *Candida sake* (e.g. strain DSM 70763), *Candida silvicola* (e.g. strain DSM 70764), *Candida solani* (e.g. strain DSM 3315), *Candida* sp. (e.g. strain DSM 1247), *Candida spandovensis* (e.g. strain DSM 70866), *Candida succiphila* (e.g. strain DSM 2149), *Candida utilis* (e.g. strains DSM 2361, 70163 or 70167), *Candida valida* (e.g. strains DSM 70169, 70178, 70179), *Candida versatilis* (e.g. strain DSM 6956), *Candida vini* (e.g. strain DSM 70184) and *Candida zeylanoides* (e.g. strain DSM 70185).

In the process according to the invention, particular preference is given to using lipases from yeasts of the *Candida* genus, especially from *Candida antarctica*. In a specific embodiment, lipase B from *Candida antarctica* is used. Preference is given to the immobilized form of this lipase, for example the lipase B from *Candida antarctica* immobilized on acrylic resin, which is commercially available, for example, under the name "Novozym 435®".

The acylating agents used in process A or in step (i) of process B are preferably selected from those in which the acid component bears an electron-rich heteroatom which is, for example, selected from fluorine, nitrogen, oxygen and sulfur atoms, adjacent to the carbonyl carbon atom. The acylating agent is preferably an ester. The acylating agent is more preferably selected from esters whose acid component bears an oxygen-, nitrogen-, fluorine- or sulfur-containing group in the α, β or γ position to the carbonyl carbon atom. Particular preference is given to those acylating agents in which the heteroatom itself is bonded in α, β or γ position and especially in the α position to the carbonyl carbon atom.

The oxygen-containing group is, for example, a hydroxyl group or an alkoxy group. The nitrogen-containing group is, for example, an amino group, while the sulfur-containing group may be the thiol group (SH) or a thioalkyl group.

The alcohol component of the ester derives preferably from linear or branched $C_1$-$C_{10}$-alcohols which may be substituted or preferably unsubstituted. However, the alcohol component more preferably derives from secondary alcohols such as isopropanol, 2-butanol, 2- or 3-pentanol and the like. It especially derives from isopropanol.

Particularly suitable esters are those of the formula V

(V)

in which
$R^1$ is $C_1$-$C_{10}$-alkyl,
$R^2$ is hydrogen or $C_1$-$C_{10}$-alkyl,
$R^3$ is hydrogen, $C_1$-$C_{10}$-alkyl or phenyl which is optionally substituted by $NH_2$, OH, $C_1$-$C_4$-alkoxy or halogen,
X is O, S or $NR^4$,
$R^4$ is hydrogen, $C_1$-$C_{10}$-alkyl or phenyl which is optionally substituted by $NH_2$, OH, $C_1$-$C_4$-alkoxy or halogen, and
a is 0, 1 or 2.

$R^1$ is preferably linear or branched $C_1$-$C_4$-alkyl. $R^1$ more preferably derives from secondary alcohols and is accordingly more preferably a $C_3$-$C_4$-alkyl group bonded via a tertiary carbon atom, such as isopropyl or 2-butyl. In particular, $R^1$ is isopropyl.

X is preferably O.

$R^2$ is preferably hydrogen or $C_1$-$C_4$-alkyl and especially hydrogen.

$R^3$ is preferably $C_1$-$C_4$-alkyl, more preferably methyl or ethyl and especially methyl.

In the context of the present invention, $C_1$-$C_4$-alkyl is a linear or branched alkyl radical having from 1 to 4 carbon atoms, such as methyl, ethyl, propyl, isopropyl, n-butyl, sec-butyl, isobutyl or tert-butyl.

$C_1$-$C_6$-Alkyl is a linear or branched alkyl radical having from 1 to 6 carbon atoms. Examples thereof, as well as the aforementioned $C_1$-$C_4$-alkyl radicals, are pentyl, neopentyl and hexyl.

$C_1$-$C_{10}$-Alkyl is a linear or branched alkyl radical having from 1 to 10 carbon atoms. Examples thereof, as well as the aforementioned $C_1$-$C_6$-alkyl radicals, are heptyl, octyl, 2-ethylhexyl, nonyl, neononyl, decyl and neodecyl.

$C_1$-$C_4$-Alkoxy is an alkyl radical which has from 1 to 4 carbon atoms and is bonded via oxygen. Examples thereof are methoxy, ethoxy, propoxy, isopropoxy, n-butoxy, sec-butoxy, isobutoxy and tert-butoxy.

$C_1$-$C_{10}$-Alcohol is an aliphatic hydrocarbon which has from 1 to 10 carbon atoms and is substituted by at least one hydroxyl group. $C_1$-$C_{10}$-Alcohol is preferably an alkane substituted by a hydroxyl radical. Examples thereof are methanol, ethanol, propanol, isopropanol, butanol, sec-butanol, isobutanol, tert-butanol, pentanol, hexanol, heptanol, octanol, 2-ethylhexanol, nonanol and decanol.

In the context of the present invention, halogen is preferably fluorine, chlorine or bromine, more preferably fluorine or chlorine.

In compounds of the formula (I-S) and (I-R) and also (II), n is preferably 0 or 2 and especially 0.

m is preferably 0 or 1 and especially 0.

The hydroxyl function in compounds (I-S) and (I-R) and the protected hydroxyl function (PO—) in compounds (II) may be in the ortho, meta or para position to the aminoalkyl group $(—(CH_2)_n—CH(NH_2)—(CH_2)_m—CH_3)$. The hydroxyl function in compounds (I-S) and (I-R) or the protected hydroxyl function (PO—) in compounds (II) is preferably in the meta or para position and especially in the para position to the aminoalkyl group.

In compounds (II), the protecting group P is preferably $C_1$-$C_6$-alkyl or a benzyl radical. P is more preferably tert-butyl or a benzyl radical and especially tert-butyl.

In the reaction in process A or in step (i) of process B, preference is given to using from 1 to 5 molar equivalents, more preferably from 1 to 4 molar equivalents and in particular from 1 to 3 molar equivalents of the acylating agent, based on the content of enantiomer of the compound of the formula (II) which is acylated. Molar equivalents shall be understood to mean the number of carboxyl groups of the acylating agent in moles which can react with 1 mol of that enantiomer of the compound (II) which is acylated. Accordingly, in the case of use of the esters of the formula (V), preference is given to using from 1 to 5 mol, more preferably from 1 to 4 mol and in particular from 1 to 3 mol of ester, based on 1 mol of enantiomer of the compound of the formula (II) which is acylated. Alternatively, in the case of use of the esters of the formula (V), preference is given to using from 0.5 to 2.5 mol, more preferably from 0.5 to 2 mol and in particular from 0.5 to 1.5 mol of ester based on 1 mol of enantiomer mixture of the formula (II).

The amount of hydrolase to be added depends upon its type and the activity of the enzyme preparation. The amount of enzyme optimal for the reaction can be determined easily by simple preliminary experiments. In general, 1000 units of hydrolase/mmole of compound (II) are used.

In a preferred embodiment, the reaction in process A or in step (i) of process B is performed in a nonaqueous reaction medium. Nonaqueous reaction media shall be understood to mean reaction media which comprise less than 1% by weight, preferably less than 0.5% by weight, of water, more preferably less than 0.1% by weight of water and in particular less than 0.05% by weight of water, based on the total weight of the reaction medium. The reaction is preferably performed in an organic solvent. Suitable solvents are, for example, aliphatic hydrocarbons, preferably having from 5 to 8 carbon atoms, such as pentane, cyclopentane, hexane, cyclohexane, heptane, octane or cyclooctane, halogenated aliphatic hydrocarbons, preferably having 1 or 2 carbon atoms, such as dichloromethane, chloroform, carbon tetrachloride, dichloroethane or tetrachloroethane, aromatic hydrocarbons such as benzene, toluene, the xylenes, chlorobenzene or dichlorobenzene, aliphatic acyclic and cyclic ethers, preferably having from 4 to 8 carbon atoms, such as diethyl ether, methyl tert-butyl ether, ethyl tert-butyl ether, dipropyl ether, diisopropyl ether, dibutyl ether, tetrahydrofuran or dioxane, or mixtures of the aforementioned solvents. Particular preference is given to using the aforementioned ethers and aromatic hydrocarbons. In particular, toluene is used.

In an alternatively preferred embodiment, the reaction in process A or in step (i) of process B is effected in bulk, i.e. without aqueous or organic solvent.

The reaction in process A or in step (i) of process B is effected generally at a reaction temperature below the deactivation temperature of the hydrolase used and preferably at least −10° C. It is more preferably in the range from 0 to 80° C., in particular from 20 to 40° C. The reaction is especially effected at room temperature.

For the performance, it is possible, for example, to initially charge the enantiomer mixture of the formula (II) with the hydrolase, the acylating agent and, if appropriate, the solvent, and to mix the mixture, for example by stirring or shaking. However, it is also possible to immobilize the hydrolase in a reactor, for example in a column, and to pass a mixture comprising the enantiomer mixture and the acylating agent through the reactor. For this purpose, the mixture can be passed through the reactor in circulation until the desired conversion has been attained. This converts the carboxyl groups of the acylating agent sequentially to amides of that enantiomer of compound (II) which is acylated enantioselectively, while the other enantiomer remains essentially unchanged. In general, the acylation will be conducted up to a conversion of at least 95%, preferably of at least 99% and in particular of at least 99.5%, based on the enantiomer of compound (II) which is present in the mixture and is acylated enantioselectively. The progress of the reaction, i.e. the sequential amide formation, can be monitored by customary methods such as gas chromatography or HPLC (High Performance Liquid Chromatography).

The enantiomer mixture (II) used is generally the racemate of the amines; mixtures in which one of the enantiomers is enriched are, however, also suitable.

The reaction mixture can be worked up in a customary manner, for example by first removing the hydrolase from the reaction mixture, for example by filtering it off or centrifuging it off, if appropriate removing the solvent from the filtrate or centrifugate, and then subjecting the residue to a separating operation.

The enantioselective conversion of the enantiomer mixture of the formula (II) forms a reaction product which comprises essentially an acylated enantiomer (i.e. amide) of compound (II) and the essentially unacylated opposite enantiomer. This mixture of amine and amide which is now present can be separated easily by customary methods. Suitable separating operations are, for example, extraction, distillation, crystallization or chromatography. Preference is given to separating the amine and the amide by distillation. In an alternatively preferred separation process, the reaction mixture dissolved or suspended in an organic solvent is admixed with an acid, which forms and precipitates the ammonium salt of the unacylated enantiomer. This can then be removed by filtration or centrifugation from the supernatant which comprises the amide of the one enantiomer of compound (II). Suitable acids are, for example, mineral acids such as hydrochloric acid, hydrobromic acid, sulfuric acid or nitric acid. However, organic acids are also suitable, for example trifluoroacetic acid or trifluoromethanesulfonic acid, although preference is given to mineral acids and especially sulfuric acid. The acid is preferably used in such an amount that those protecting groups P of the OH function which are typically detached by acid treatment are not removed. This is especially true in the case of use of tert-butyl as the protecting group. Preference is given to using the acid in about an equimolar amount relative to the unacylated enantiomer, for example in an amount of from 0.9 to 1.5 mol, preferably from 1 to 1.2 mol and especially about 1 mol, based on 1 mol of the unacylated enantiomer. In the case of polyprotic acids such as sulfuric acid, the molar ratios relate of course to the number of protons present in the acid.

In step (iii), the essentially unacylated enantiomer of compound (II) removed in step (ii) is finally deprotected and converted to the corresponding free, essentially enantiomerically pure amine. In particular, the unacylated enantiomer removed in step (ii) is the S enantiomer of compound (II), which is deprotected in step (iii) and converted to compound (I-S).

The deprotection is effected generally under the reaction conditions as known from the prior art for the detachment of the particular protecting group P. Suitable deprotecting processes are described, for example, in T. W. Greene, P. G. M. Wuts, Protective Groups in Organic Synthesis, 3rd Edition, Wiley Interscience 1999, or in P. J. Kocienski, Protective Groups, Thieme 2000, which are hereby fully incorporated by reference.

For instance, the tert-butyl protecting group is detached preferably by treating the protected compound with an acid. Suitable acids are the abovementioned mineral and organic acids. Preferred acids are mineral acids such as hydrochloric acid and sulfuric acid. Preference is given to effecting the deprotecting operation with acids at elevated reaction temperatures, for example at from 50 to 150° C., preferably from 70 to 100° C.

When a benzylic protecting group P has been used, the benzyl component is detached preferably by hydrogenolysis. The hydrogenolysis is effected generally under known conditions, for example using a suitable hydrogenation catalyst such as palladium, palladium hydroxide or platinum.

When the amine, after the protecting group detachment, is still present in the form of the ammonium salt, for example because the protected product has been deprotected with acids or because the removal in step (ii) has been effected by precipitating the ammonium salt, the amine is released from the ammonium salt by means of a suitable base. Suitable bases are, for example, alkali metal hydroxides such as sodium hydroxide or potassium hydroxide, alkaline earth metal hydroxides such as calcium hydroxide or magnesium hydroxide, alkali metal carbonates or alkaline earth metal carbonates such as sodium carbonate, potassium carbonate or calcium carbonate. Preference is given to using alkali metal hydroxides such as sodium hydroxide or potassium hydroxide. Preference is given to effecting the neutralization in an aqueous medium. For easier isolation of the amine, the base is preferably used in such an amount that, on the one hand, the amine function is neutralized, but, on the other hand, the hydroxyl function on the phenol ring is not deprotonated and the neutral molecule is precipitated. Accordingly, the pH is preferably adjusted to the isoelectric point. The free amine obtained can subsequently, if desired, be subjected to further purification steps.

The other enantiomer, whose protected derivative has been acylated enantioselectively in process A or in step (i) of process B, can be obtained by hydrolyzing the essentially acylated enantiomer of compound (II) obtained in step (ii) with detachment of the acyl function to obtain the corresponding enantiomer of compound (II). The enantiomer is preferably the R enantiomer of compound (II).

The hydrolysis is effected generally under reaction conditions as known for the hydrolysis of amides. Reaction conditions are described, for example, in DE-A-19534208 or in Organikum, VEB Deutscher Verlag der Wissenschaften, Berlin 1988, 17th ed., p. 419, or in Jerry March, Advanced Organic Chemistry, 3rd ed., John Wiley and Sons, p. 338 ff., which are hereby fully incorporated by reference. Preference is given to effecting the hydrolysis to the amine by reacting with a base. Suitable bases are, for example, alkali metal hydroxides such as sodium hydroxide and potassium hydroxide, alkaline earth metal hydroxides such as calcium hydroxide, alkali metal and alkaline earth metal carbonates such as sodium carbonate, potassium carbonate and calcium carbonate, ammonia, amines such as dimethylamine, diethylamine, trimethylamine, diethylamine, triethylamine, diisopropylamine and diisopropylethylamine, or amino alcohols such as ethanolamine, diethanolamine and triethanolamine. Particular preference is given to using the alkali metal hydroxides mentioned, if appropriate in combination with an amine or amino alcohol. The hydrolysis can be performed in water or in a solvent or in a mixture of water and solvent. Suitable solvents are alcohols, preferably having from 1 to 3 carbon atoms, such as methanol, ethanol, propanol or isopropanol, glycols, especially having from 2 to 8 carbon atoms, such as ethylene glycol, di- and triethylene glycol, amines and amino alcohols, for example the aforementioned amines and amino alcohols, and also the mixtures of the aforementioned solvents, and mixtures thereof with water. The hydrolysis is effected preferably at elevated temperature, for example at the boiling point of the solvent used. The hydrolyzed enantiomer of compound (II) obtained can subsequently be deprotected under the same reaction conditions as described for the opposite enantiomer, and converted to the opposite amine (I-S) or preferably (I-R).

The process according to the invention affords the amines (I-S) and (I-R) with an enantiomeric excess (ee) of preferably at least 95%, more preferably of at least 96%, even more preferably of at least 97% and in particular of at least 98%, for example at least 99%.

Especially in the case of the compound 4-(1-aminoethyl) phenol, the process according to the invention affords the S enantiomer with an enantiomeric excess (ee) of preferably at least 98% ee, more preferably of at least 99% ee and in particular of at least 99.4% ee. The enantiomeric purity of the corresponding R enantiomer is preferably at least 98% ee and more preferably at least 99% ee.

Especially in the case of the compound 3-(1-aminoethyl) phenol, the process according to the invention affords the S enantiomer with an enantiomeric excess (ee) of preferably at least 98% ee, more preferably of at least 99% ee and in particular of at least 99.5% ee. The enantiomeric purity of the corresponding R enantiomer is preferably at least 98% ee and more preferably at least 98.5% ee.

The enantiomeric excess of the amines (I-S) and (I-R) can be determined by means of common processes, for example by determining the optical rotation or by chromatography on a chiral phase, for example by HPLC or gas chromatography using chiral columns.

When there is no interest in one of the enantiomers (I-R) or (I-S) or in reaction products thereof, it can be racemized and reused in process A or in step (i) of process B. This recycling makes it possible to obtain more than 50% of the desired enantiomer (I-S) or (I-R) overall from the enantiomer mixture (II). Suitable racemization conditions are known and are described, for example, in WO 00/209357 or WO 00/47546, which are hereby explicitly incorporated by reference.

In a preferred embodiment of the process according to the invention (A or B), the compound of the formula (II) is preferably obtained by
(a) protecting a compound of the formula (III)

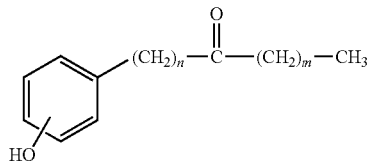

in which n and m are each as defined above on the OH group to obtain compound (IV)

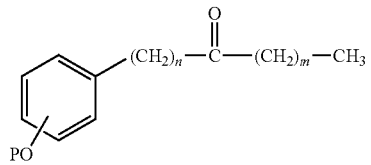

in which P is as defined above, and
(b) subjecting compound (IV) to a reductive amination to obtain the compound of the formula (II).

The reverse sequence of these steps is also conceivable, i.e. first reductive amination of the compound (III) to obtain an amine compound VI

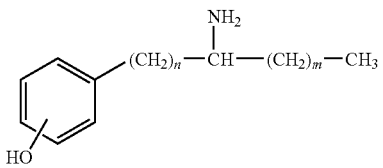

and only then introduction of the hydroxyl protecting group on the resulting amine VI to obtain the compound (II).

Suitable protecting groups P are those which, on the one hand, can be attached easily, but, on the other hand, also survive process A or steps (i) and (ii) of process B, and nevertheless can also be removed again, for example, in steps (iii) and (iv) of process B. Customary protecting groups for hydroxyl functions are the corresponding alkyl ethers, benzyl ethers and silyl ethers. They are usually obtained by reacting the appropriate alkyl halide, benzyl halide or silyl halide with the compound to be protected. In the case of compound (III), it has, however, been found to be particularly favorable to convert them to the corresponding benzyl ethers or a benzyl ether substituted on the phenyl ring of the benzyl group or in particular to the tert-butyl ether (P=benzyl, substituted benzyl or tert-butyl).

The substituted benzyl group is preferably a methyl- or dimethylbenzyl group. The advantage of using such substituted benzyl groups lies in their lower sensitivity towards hydrogenolytic conditions of step (b) compared to the unsubstituted benzyl.

The protecting group is introduced in step (a) generally under the customary reaction conditions as known from the prior art for the introduction of the appropriate protecting group. In this context, reference is made to T. W. Greene, P. G. M. Wuts, Protective Groups in Organic Synthesis, 3rd Edition, Wiley Interscience 1999, and to P. J. Kocienski, Protective Groups, Thieme 2000, which is hereby fully incorporated by reference.

For instance, compound (III) is converted to the corresponding benzyl ether, for example, by reacting (III) with a benzyl halide optionally substituted on the phenyl ring, for example with benzyl bromide or benzyl chloride, the reaction being performed generally in the presence of a base. Suitable bases are the aforementioned alkali metal and alkaline earth metal hydroxides and also alkali metal and alkaline earth metal carbonates.

The conversion to the corresponding tert-butyl ether is effected preferably by reacting compound (III) with isobutene in the presence of an acid. Suitable acids are mineral acids such as sulfuric acid, and strong organic acids such as trifluoroacetic acid or trifluoromethanesulfonic acid. Particular preference is given to using trifluoromethanesulfonic acid. The acid is used in catalytic amounts. Isobutene is used in an at least equimolar amount in relation to the compound to be protected, for example in an amount of from 1 to 10 mol based on 1 mol of the compound to be protected. However, preference is given to using it in excess. The molar ratio of isobutene to the compound to be protected is preferably from 2:1 to 10:1, more preferably from 3:1 to 7:1, for example about 5:1. The protecting group operation is effected generally in a solvent. Suitable solvents are those which enter into a reaction neither with the reactants nor with the product. Examples of solvents suitable for this purpose are those mentioned for step (i). Preference is given to using halogenated alkanes such as methylene chloride, chloroform, carbon tetrachloride or dichloroethane. The reaction temperature is typically from −80 to 40° C., more preferably from −50 to 30° C. and especially about room temperature. The reaction can be effected either at ambient pressure or under elevated pressure. In the case of performance under ambient pressure, the procedure is generally to first condense isobutene by cooling to below −7° C. and then to react it with compound (III) in the presence of the acid catalyst and of the solvent at the desired reaction temperature. In the case of performance under pressure, isobutene need not be condensed. The pressure is preferably from 1.5 to 20 bar, more preferably from 2 to 20 bar.

The protected compound (IV) is subsequently isolated by customary processes and, if appropriate, purified. For example, the reaction solution, preferably after the removal of excess isobutene, can first be neutralized, for example by stirring with a basic aqueous solution and/or by extraction with water or an aqueous basic solution, drying the organic solvent phase and removing the solvent. If desired, the product (IV) can be purified further, for example by chromatography or extraction.

Subsequently, the protected product (IV) is subjected to a reductive amination to give the racemic amine (II). Suitable reaction conditions for reductive aminations are described, for example, in Jerry March, Advanced Organic Chemistry, 3rd ed., John Wiley and Sons, p. 798 ff., which is hereby fully incorporated by reference. The aminating and reducing components used are preferably ammonia and hydrogen. However, the reaction is also possible with other reducing agents such as ammonia in combination with zinc and HCl, sodium cyanoborohydride ($NaBH_3CN$), sodium borohydride, iron pentacarbonyl with alcoholic KOH, or selenophenol (Ph-SeH). However, preference is given to using ammonia in combination with hydrogen. In this case, the reaction is effected generally in the presence of a hydrogenation catalyst, in which case the hydrogenation catalyst can be either homogeneous or heterogeneous.

When the protecting group introduced in step (a) is a benzyl group, the hydrogenation catalyst is preferably selected such that it allows very mild reaction conditions, and the hydrogenolytic detachment of the benzyl protecting group in the course of the reductive amination is thus prevented. Alternatively, a different reducing agent, for example sodium cyanoborohydride, is used instead of hydrogen in the presence of a benzyl protecting group.

Suitable hydrogenation catalysts under the above proviso are all prior art catalysts which catalyze the reductive amination of ketones and aldehydes to the corresponding amines. The hydrogenation catalysts preferably comprise at least one metal of group VIII.

Particularly suitable metals of group VIII are selected from ruthenium, cobalt, rhodium, nickel, palladium and platinum.

The metals may also be used in the form of mixtures. Moreover, the catalysts may comprise, in addition to the metals of group VIII, also small amounts of further metals, for example metals of group VIIa, in particular rhenium, or metals of group Ib, i.e. copper, silver or gold. Particularly preferred metals of group VIII are ruthenium, nickel, palladium and platinum, in particular ruthenium, nickel and palladium, and more preferably ruthenium and nickel. The catalyst especially comprises nickel as the catalytically active species.

When a heterogeneous catalyst is used, it is suitably present in finely divided form. The finely divided form is achieved, for example, as follows:

a) Black catalyst: shortly before use as a catalyst, the metal is deposited reductively from the solution of one of its salts.
  b) Adams catalyst: the metal oxides, in particular the oxides of platinum and palladium, are reduced in situ by the hydrogen used for the hydrogenation.
  c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.
  d) Supported catalyst: black catalysts can also be precipitated on the surface of a support substance. Suitable supports and support materials are described below.

Such heterogeneous catalysts are described in general form, for example, in Organikum, 17th edition, VEB Deutscher Verlag der Wissenschaften, Berlin, 1988, p. 288.

The supports may consist of metallic or nonmetallic, porous or nonporous material.

Suitable metallic materials are, for example, highly alloyed stainless steels. Suitable nonmetallic materials are, for example, mineral materials, for example natural and synthetic minerals, glasses or ceramics, plastics, for example synthetic or natural polymers, or a combination of the two.

Preferred support materials are carbon, in particular activated carbon, silicon dioxide, in particular amorphous silicon dioxide, alumina, and also the sulfates and carbonates of the alkaline earth metals, calcium carbonate, calcium sulfate, magnesium carbonate, magnesium sulfate, barium carbonate and barium sulfate.

The catalyst may be applied to the support by customary processes, for example by impregnating, wetting or spraying the support with a solution which comprises the catalyst or a suitable precursor thereof.

Suitable supports and processes for applying the catalyst thereto are described, for example, in DE-A-10128242, which is hereby fully incorporated by reference.

It is also possible to use homogeneous hydrogenation catalysts in the process according to the invention. Examples thereof are the nickel catalysts which are described in EP-A-0668257. However, disadvantages of use of homogeneous catalysts are their preparation costs and also the fact that they generally cannot be regenerated.

Therefore, preference is given to using heterogeneous hydrogenation catalysts in the process according to the invention.

The metal is more preferably used in supported form or as metal sponge. Examples of supported catalysts are in particular palladium, nickel or ruthenium on carbon, in particular activated carbon, silicon dioxide, in particular on amorphous silicon dioxide, barium carbonate, calcium carbonate, magnesium carbonate or alumina, and the supports may be present in the above-described shapes. Preferred support shapes are the above-described shaped bodies.

The metallic catalysts may also be used in the form of their oxides, in particular palladium oxide, platinum oxide or nickel oxide, which are then reduced under the hydrogenation conditions to the corresponding metals.

The metal sponge used is in particular Raney nickel.

The hydrogenation catalyst used in the process according to the invention is especially Raney nickel.

The amount of catalyst to be used depends on factors including the particular catalytically active metal and its use form, and may be determined in the individual case by those skilled in the art.

The reductive amination is effected at a temperature of preferably from 20 to 200° C., more preferably from 50 to 150° C. and in particular from 70 to 120° C.

The reaction pressure of the reductive amination is preferably in the range from 2 to 300 bar, more preferably from 50 to 150 bar.

Both reaction pressure and reaction temperature depend upon factors including the activity and amount of the hydrogenation catalyst used and may be determined by the person skilled in the art in the individual case.

The reductive amination of step (b) can be effected in a suitable solvent. Suitable solvents are, with the exception of the halogenated hydrocarbons, those mentioned above for step (i). However, preference is given to effecting the reaction in the absence of an organic solvent. Instead, in a preferred embodiment, condensed ammonia which is used in excess is used as the solvent.

After the reaction has ended and the reaction vessel has been decompressed, excess ammonia is generally evaporated off and the catalyst is removed. The heterogeneous catalyst is preferably removed by filtration or by sedimentation and removal of the upper, product-containing phase. Other removal processes for removing solids from solutions, for example centrifugation, are also suitable for removing the heterogeneous catalysts. Homogeneous catalysts are removed by customary processes for separating identical-phase mixtures, for example by chromatographic methods. If appropriate, it may, depending on the catalyst type, be necessary to deactivate it before the removal. This can be effected by customary processes, for example by washing the reaction solution with protic solvents, for example with water or with $C_1$-$C_3$-alkanols such as methanol, ethanol, propanol or isopropanol, which have been basified or acidified if required. If a solvent has been used in the reaction, it is generally likewise removed, which can be effected by customary processes, for example by distillation, especially under reduced pressure.

The reaction product can be purified by customary processes, for example by distillation, sublimation, extraction or chromatography.

In the case of performance of the reaction in reverse sequence, i.e. first reductive amination and only then protecting group introduction, the statements made above apply to the step of reductive amination, except that the problem of detachment of particular protecting groups under the amination conditions does not exist. However, a benzyl protecting group cannot be used in this reaction sequence, since it would react preferentially with the amino group obtained, and a benzylamine which has formed is also more difficult to deprotect than a benzyl ether. Preference is given here to using an alkyl ether and specifically a tert-butyl ether as the protecting group. For the introduction of the protecting group, the statements made above apply, and it should be noted in the case of reaction under acid catalysis that the acid has to be used in a more than equimolar amount in relation to the compound to be protected, since it is bound at least partly by the amino function.

Preference is given to preparing compound (II) in the sequence of steps (a) and then (b).

In compounds (III), (IV) and (VI) too, n is preferably 0 or 2 and in particular 0. m is preferably 0 or 1 and in particular 0. In these compounds too, the hydroxyl function (in compounds (III) and (VI)) or the protected hydroxyl function PO (in compound (IV)) may be in the ortho, meta or para position to the alkylcarbonyl group or aminoalkyl group. The hydroxyl function or the protected hydroxyl function PO is preferably in the meta or para position and in particular in the para position to the alkylcarbonyl group or aminoalkyl group.

Finally, the invention provides a process for preparing optically active compounds of the formulae I-S and/or I-R

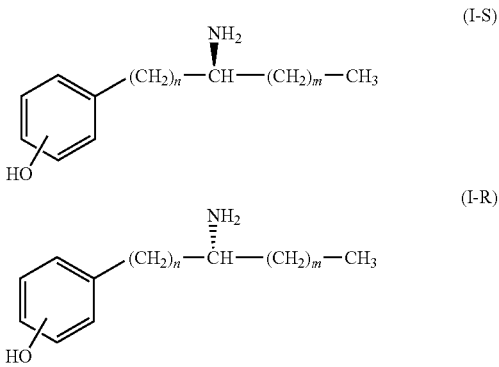

in which n and m are each as defined above, by
(a) protecting a compound of the formula (III)

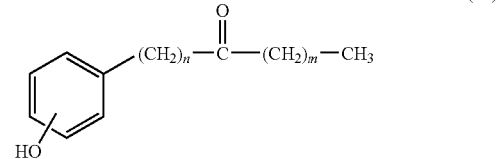

on the OH group to obtain compound (IV)

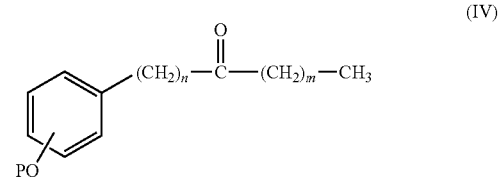

in which P is as defined above;
(b) subjecting compound (IV) to a reductive amination to obtain an enantiomer mixture of the formula (II)

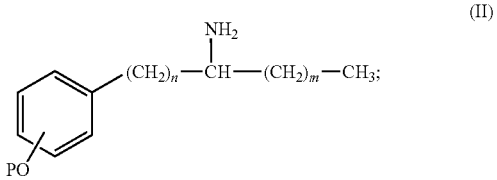

(c) reacting the enantiomer mixture of the formula (II) with an acylating agent in the presence of a hydrolase to obtain a mixture in which one enantiomer is present essentially in the acylated form and the other enantiomer is present essentially in the unacylated form;

(d) removing the unacylated enantiomer of compound (II) from the mixture obtained in step (i);

(e) deprotecting the unacylated enantiomer of compound (II) obtained in step (ii) to give the amine (I-S) or (I-R); and (f) if desired, hydrolyzing the essentially acylated enantiomer of compound (II) obtained in step (i) to the corresponding unacylated enantiomer of the amine (II) and then deprotecting it to the amine (I-R) or (I-S).

The remarks made above regarding suitable and preferred embodiments of the invention and of the process apply here correspondingly.

The process according to the invention, especially in that embodiment which comprises steps (a) and (b), affords the compounds (I-S) and/or (I-R) in high yields and with a very high enantiomeric purity.

The present invention is illustrated by the nonrestrictive examples which follow.

EXAMPLES

1. Synthesis of (S)-4-(1-aminoethyl)phenol and (R)-4-(1-aminoethyl)phenol

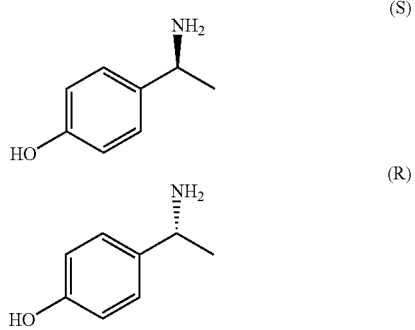

1.1 Introduction of the Protecting Group: Conversion of 4-hydroxyacetophenone to 4-tert-butoxyacetophenone In a three-neck flask with dry-ice condenser, p-hydroxyacetophenone (60 g, 0.44 mol) in methylene chloride (800 ml) was admixed with 3 drops of trifluoromethanesulfonic acid. Condensed isobutene (123 g, 2.2 mol) was added to the reaction mixture, in the course of which cloudiness appeared and a finely crystalline solid precipitated out. The slightly violet mixture was stirred overnight with the dry-ice condenser attached, in the course of which dry ice and excess isobutene evaporated off. The next day, the mixture was added to semi-concentrated sodium carbonate solution (600 ml) with stirring. After the phase separation, the organic phase was washed with semisaturated sodium carbonate solution a sufficient number of times for the aqueous phase to remain colorless. The organic phase was dried over sodium sulfate and the solvent was removed under reduced pressure. 66 g (78% of theory) of 4-tert-butoxyacetophenone were obtained as a colorless oil, which, according to GC analysis, had a purity of 99.9%.

$^1$H NMR (400 MHz; CDCl$_3$): δ=1.40 (s, 9H); 2.58 (s, 3H); 7.05 and 7.90 (AA',BB' system; J$_{AB}$=10.5 Hz, 4H).

1.2 Reductive Amination: Synthesis of 1-(4-tert-butoxyphenyl)ethylamine

A mixture of 4-tert-butoxyacetophenone from example 1.1 (44 g, 0.23 mol) which had been stabilized with 5 drops of concentrated ammonia solution, and 1 g of Raney nickel were admixed with 3 drops of glacial acetic acid and dissolved in liquid ammonia (100 ml) in an autoclave. The reaction mixture was heated to 80° C. and hydrogen was introduced up to an internal pressure of 100 bar. Subsequently, the mixture was stirred at 100° C. until no further hydrogen was taken up (10-20 h). The autoclave was decompressed, the residue was taken up in methanol (200 ml) after the ammonia had evaporated off, and the catalyst was filtered through kieselguhr. The filtrate was concentrated and the remaining distillation residue was recondensed in an oil-pump vacuum at 85° C. 40 g (90% of theory) of crude amine were obtained, which, according to GC analysis, had a purity of 95.6%. The condensates from several batches were subjected collectively to a vacuum distillation. 1-(4-tert-Butoxyphenyl)ethylamine was obtained in a yield of 75% of theory as the pure product.

Boiling point: 94-97° C. (0.4 mm)

$^1$H NMR (400 MHz; CDCl$_3$): δ=1.65 (s, 9H); 1.80 (d, J=7 Hz, 3H); 4.20 (q, J=7 Hz, 1H); 4.40 (s, broad, 2H); 6.80 and 7.50 (AA',BB' system; J$_{AB}$=10.5 Hz, 4H).

1.3 Optical Resolution 1-(4-tert-Butoxyphenyl)ethylamine (246 g, 1.28 mol) was admixed with isopropyl methoxyacetate (254 g, 1.92 mol) and Novozyme® 435 (2.5 g), and stirred at room temperature. After one hour, a white, finely crystalline residue precipitated out. After the mixture had been heated to 35° C., it was stirred at this temperature overnight. The subsequent analysis of the optical purity showed that the S enantiomer of 1-(4-tert-butoxyphenyl)ethylamine was enantiomerically pure. The acylated R enantiomer had an optical purity of 98.9%. The mixture was filtered through kieselguhr and washed with toluene (200 ml), and the filtrate was concentrated at 40° C. on a rotary evaporator. The residue was taken up in toluene (400 ml) and admixed dropwise with 38% sulfuric acid (82 g, 0.31 mol). A white thick precipitate formed, which was diluted with toluene (500 ml). The solid was filtered off with suction, washed with toluene (300 ml) and dried at 40° C. in a vacuum drying cabinet overnight. 144.4 g (96%) of the sulfate salt of (S)-1-(4-tert-butoxyphenyl)ethylamine were obtained.

To isolate the acylated R enantiomer of 1-(4-tert-butoxyphenyl)ethylamine, the water phase of the combined filtrates was removed and the organic phase was concentrated until a white greasy solid (256 g) remained. The solid was melted and freed of all volatile constituents in an oil-pump vacuum at a bath temperature of 70° C. 180 g (quantitative yield) of crude (R)—N-1-(4-tert-butoxyphenyl)ethylmethoxyacetamide were obtained, which was still contaminated by isopropyl methoxyacetate (approx. 5%). The optical purity was 98.9% ee.

$^1$H NMR of (R)—N-1-(4-tert-butoxyphenyl)ethylmethoxyacetamide $^1$H NMR (400 MHz; CDCl$_2$: δ=1.30 (s, 9H); 1.50 (d, J=7 Hz, 3H); 3.40 (s, 3H); 3.87 and 3.95 (AB system; J$_{AB}$=16 Hz, 2H); 5.15 (dq, J=7 Hz and 9 Hz, 1H); 6.70 (s, broad, 1H); 6.95 and 7.20 (AA', BB' system; J$_{AB}$=10.5 Hz, 4H).

1.4 Amide Hydrolysis: Synthesis of (R)-1-(4-tert-butoxyphenyl)ethylamine (R)—N-1-(4-tert-Butoxyphenyl)ethylmethoxyacetamide from example 1.3 (180 g with a purity of 94%; corresponds to 0.64 mol of pure substance) was mixed with triethanolamine (20 ml) with stirring and then admixed with 50% NaOH (70.8 g, 0.89 mol). The mixture was then stirred at a bath temperature of 140° C. for another seven hours, after which all of the amide had been converted according to GC. The mixture was diluted with water (100 ml), cooled and extracted with tert-butyl methyl ether (3×100 ml). The combined extracts were washed with saturated sodium chloride solution (50 ml) and dried over Na$_2$SO$_4$. After the solvent had been removed on a rotary evaporator, 123.7 g (73%) of (R)-1-(4-tert-butoxyphenyl)ethylamine were obtained in the form of a pale brownish oil. The chemical purity was 99.4%, the optical purity 98.9% ee.

The $^1$H NMR spectrum is identical to that reported in example 1.2.

1.5 Detachment of the Protecting Group: Synthesis of (R)-4-(1-aminoethyl)phenol (R)-1-(4-tert-Butoxyphenyl)ethylamine (89.4 g, 0.463 mol) was dissolved in 10% hydrochloric acid (200 ml) and heated to 85° C. At approx. 80° C., vigorous gas evolution set in. The mixture was stirred at 85° C. for another three hours, after which the gas evolution had stopped. The pale yellow mixture was allowed to cool to room temperature and then 20% NaOH was added dropwise up to a pH of 10.2. The deprotected phenol precipitated out overnight in the form of a pale yellow powder. It was filtered off with suction and dried in a drying cabinet overnight. For purification, the crude product was digested with tert-butyl methyl ether (200 ml). The suspension was filtered and the filter residue was dried again under reduced pressure. 51.3 g (63%) of (R)-4-(1-aminoethyl)phenol were obtained in the form of a pale yellow powder.

M.p.: 121° C.

Rotation [α]$_D$=27.5° (c=1 in methanol).

$^1$H NMR (400 MHz; DMSO-d$_6$): δ=1.15 (d, J=7 Hz, 3H); 1.75 (s, broad, 2H); 3.90 (q, J=7 Hz, 1H); 6.65 and 7.15 (AA',BB' system; J$_{AB}$=10.5 Hz, 4H); 9.20 (s, broad, 1H).

1.6 Detachment of the Protecting Group: Synthesis of (S)-4-(1-aminoethyl)phenol (S)-1-(4-tert-Butoxyphenyl)ethylammonium sulfate from example 1.3 (144 g, 0.61 mol) was suspended in water (500 ml). The suspension was adjusted to a pH of 1 by adding conc. H$_2$SO$_4$ (3 ml) and heated to 85° C. Gentle gas evolution set in. After three hours, all of the salt had gone into solution and the gas evolution had stopped. The mixture was allowed to cool and admixed with 20% NaOH until the pH was 10.2. The next day, the solid which had precipitated out overnight was filtered off with suction and dried in a vacuum drying cabinet. Since the crude product still comprised insoluble sodium sulfate, it was taken up in methanol (1500 ml) and the insoluble Na$_2$SO$_4$ was filtered off. The filtrate was concentrated and the residue was digested with tert-butyl methyl ether (200 ml). After the solid had been filtered off with suction and dried under reduced pressure, 68 g (58% of theory) of (S)-4-(1-aminoethyl)phenol were obtained in the form of a pale yellow powder.

M.p.: 120° C.

Rotation [α]$_D$=−28° (c=1 in methanol).

The $^1$H NMR spectrum of the product is identical to that reported in example 1.5.

2. Synthesis of (S)-3-(1-aminoethyl)phenol and (R)-3-(1-aminoethyl)phenol

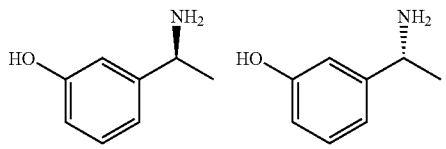

2.1 Introduction of the Protecting Group: Conversion of 3-hydroxyacetophenone to 3-tert-butoxyacetophenone In a three-neck flask with dry-ice condenser, metahydroxyacetophenone (50 g, 0.37 mol) in methylene chloride (1 l) was admixed with 3 drops of trifluoromethanesulfonic acid. Condensed isobutene (103 g, 1.84 mol) was added to the reaction mixture, in the course of which cloudiness appeared and a finely crystalline solid precipitated out. The pale yellow mixture was stirred overnight (16 h) with the dry-ice condenser attached, in the course of which dry ice and excess isobutene evaporated off. The next day, the orange mixture was added with stirring to semiconcentrated sodium carbonate solution (500 ml). After the phase separation, the organic phase was washed 4 times with 150 ml each time of semisaturated sodium carbonate solution until the aqueous phase remained colorless. The organic phase was dried over sodium sulfate and the solvent was removed under reduced pressure. 60 g (87% of theory) of 3-tert-butoxyacetophenone were obtained as a colorless oil, which, according to GC analysis, had a purity of 95%.

$^1$H NMR (400 MHz; CDCl$_3$): δ=1.40 (s, 9H); 2.58 (s, 3H); 7.20 (m, 1H); 7.35 (dd; J=10 and 12 Hz, 1H); 7.58 (m, 1H), 7.68 (m, 1H).

2.2 Reductive Amination: Synthesis of 1-(3-tert-butoxyphenyl)ethylamine

A mixture of 3-tert-butoxyacetophenone from example 2.1 (60 g, 0.32 mol), which had been stabilized with 5 drops of concentrated ammonia solution, and 1 g of Raney nickel were admixed with 3 drops of glacial acetic acid, and dissolved in liquid ammonia (100 ml) in an autoclave. The reaction mixture was heated to 80° C. and hydrogen was introduced up to an internal pressure of 100 bar. Subsequently, the mixture was stirred at 100° C. until no further hydrogen was taken up (10-20 h). The autoclave was decompressed, the residue was taken up in methanol (200 ml) after the ammonia had evaporated off, and the catalyst was filtered off through kieselguhr. The filtrate was concentrated and the remaining distillation residue was recondensed in an oil-pump vacuum at 85° C. 57.4 g (93% of theory) of crude amine were obtained, which, according to GC analysis, had a purity of 91%. The condensates from several batches were subjected collectively to a vacuum distillation. 1-(3-tert-Butoxyphenyl)ethylamine was obtained in a yield of 72% of theory as the pure product.

Boiling point: 89-90° C. (0.4 mm)

$^1$H NMR (400 MHz; CDCl$_3$): δ=1.35 (s, 9H); 1.38 (d, J=7 Hz, 3H); 1.58 (s, broad, 2H); 4.10 (m, 1H); 6.88 (m, 1H); 6.95 (m, 1H); 7.05 (m, 1H); 7.20 (dd; J=10 and 12 Hz, 1H).

2.3 Optical Resolution 1-(3-tert-Butoxyphenyl)ethylamine (86 g, 0.45 mol) was admixed with isopropyl methoxyacetate (129 g, 0.98 mol) and Novozyme® 435 (0.9 g), and stirred at room temperature for 16 h. The subsequent analysis of the optical purity showed that the S enantiomer of 1-(3-tert-butoxyphenyl)ethylamine was enantiomerically pure. The acylated R enantiomer had an optical purity of 99.1%. The mixture was filtered through kieselguhr and washed with toluene (200 ml), and the filtrate was concentrated at 40° C. on a rotary evaporator. The residue was taken up in toluene (200 ml) and admixed dropwise with 37% sulfuric acid (29.5 g, 0.12 mol). A greasy, unfilterable precipitate formed, which was dissolved in water (250 ml). The aqueous solution was washed 3 times with 50 ml each time of toluene. The combined organic phases were washed once with 50 ml of water and then dried over sodium sulfate. After the solvent had been removed, the residue was freed of further volatile constituents in an oil-pump vacuum at 0.5 bar and 85° C. 70 g of crude (R)—N-1-(3-tert-butoxyphenyl) ethylmethoxyacetamide were obtained, whose chemical purity, according to GC analysis, was 93%. The optical purity was 99% ee.

To isolate (S)-1-(3-tert-butoxyphenyl)ethylamine, the combined aqueous phases were adjusted to pH 14 by adding solid sodium hydroxide. Subsequently, toluene (100 ml) was added, the phases were separated and the aqueous phase was extracted 3 times more with 50 ml of toluene each time. The combined organic phases were dried over sodium sulfate and freed of the solvent under reduced pressure. 40.9 g (94%) of pure (S)-1-(3-tert-butoxyphenyl)ethylamine were obtained as a colorless oil having an enantiomic purity of above 99.9% ee.

$^1$H NMR of (R)—N-1-(3-tert-butoxyphenyl)ethylmethoxyacetamide:

$^1$H NMR (400 MHz; CDCl$_3$): δ=1.35 (s, 9H); 1.52 (d, J=7 Hz, 3H); 3.40 (s, 3H); 3.90 and 3.95 (AB system; J$_{AB}$=16 Hz, 2H); 5.15 (dq, J=7 Hz and 9 Hz, 1H); 6.80 (s, broad, 1'-1); 6.92 (m, 1H); 6.95 (m, 1H); 7.05 (m, 1H); 7.25 (dd; J=10 and 12 Hz, 1H).

2.4 Amide Hydrolysis: Synthesis of (R)-1-(3-tert-butoxyphenyl)ethylamine (R)—N-1-(3-tert-Butoxyphenyl)ethylmethoxyacetamide from example 2.3 (63.5 g with a purity of 93%; corresponds to 0.22 mol of pure substance) was mixed with triethanolamine (6 ml) with stirring and then admixed with 50% NaOH (23.2 g, 0.29 mol). The mixture was then stirred at a bath temperature of 140° C. for another 16 hours, after which all of the amide had reacted according to GC analysis. The mixture was diluted with water (100 ml), cooled and extracted with tert-butyl methyl ether (3×100 ml). The combined extracts were washed with saturated sodium chloride solution (50 ml) and dried over Na$_2$SO$_4$. After the solvent had been removed on a rotary evaporator, 41 g (92%) of (R)-1-(3-tert-butox-yphenyl)ethylamine were obtained in the form of a colorless oil. The chemical purity was 99.4%, the optical purity 98.9% ee.

The $^1$H NMR spectrum is identical to that reported in example 2.2.

2.5 Detachment of the Protecting Group: Synthesis of (R)-3-(1-aminoethyl)phenol (R)-1-(3-tert-Butoxyphenyl)ethylamine (5 g, 25.9 mmol) was suspended in water (10 ml) and admixed with 38% sulfuric acid up to a pH of 1. The mixture was heated to 85° C. and stirred at this temperature for another three hours, after which the gas evolution had stopped. The colorless mixture was allowed to cool to room temperature and then 20% NaOH was added dropwise up to a pH of 9.1, whereupon the protected phenol precipitated out in the form of a white powder. This was filtered off with suction and dried overnight in a drying cabinet. 2.6 g (73%) of (R)-3-(1-aminoethyl)phenol were obtained in the form of a pale yellow powder.

M.p.: 160° C.

Rotation [α]$_D$, =22.5° (c=1 in methanol).

$^1$H NMR (400 MHz; CDCl$_3$): δ=1.35 (d, J=7 Hz, 3H); 2.15 (s, broad, 3H); 4.05 (q, J=7 Hz, 1H); 6.75 (m, 1H); 6.50 (m, 2H); 7.15 (m, 1H).

2.6 Detachment of the Protecting Group: Synthesis of (S)-3-(1-aminoethyl)phenol The protecting group was detached from (S)-1-(3-tert-butoxyphenyl)ethylamine from example 2.3 analogously to example 2.5. Pure (S)-3-(1-aminoethyl)phenol was obtained in a yield of 78% of theory and an enantiomeric purity of above 99.9% ee.

Rotation [α]$_D$=22.4° (c=1 in methanol).

The $^1$H NMR spectrum is identical to that reported in example 2.5.

The invention claimed is:

1. A process for preparing optically active compounds of formulae I-S and/or I-R

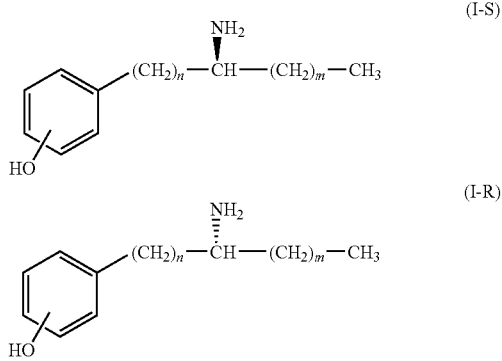

wherein n is 0, 1, or 2; and m is 0, 1, or 2;

comprising (i) reacting an enantiomer mixture of compounds of formula II

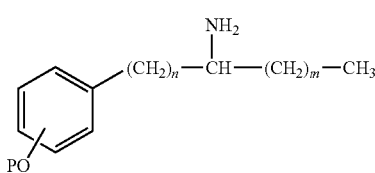

wherein
P is a tert-butyl group or a benzyl group optionally substituted on the phenyl ring;
with an acylating agent in the presence of a hydrolase to obtain a mixture wherein one enantiomer of the mixture of compounds of formula (II) is present essentially in acylated form and the other enantiomer of the mixture of compounds of formula (II) is present essentially in the unacylated form;
(ii) removing the unacylated enantiomer of compound (II) from the mixture obtained in step (i);
(iii) deprotecting the unacylated enantiomer of compound (II) obtained in step (ii) to give the amine (I-S) or (I-R); and
(iv) if desired hydrolyzing the essentially acylated enantiomer of compound (II) obtained in step (i) to give the corresponding unacylated enantiomer of the amine (II) and subsequently deprotecting it to give the amine (I-R) or (I-S).

2. The process of claim 1, wherein the essentially unacylated enantiomer obtained in (i) is the S enantiomer of the compounds of formula (II), and the essentially acylated enantiomer is the R enantiomer of the compounds of formula (II).

3. The process of claim 1, wherein the acylating agent is selected from esters whose acid component bears an oxygen-, nitrogen-, fluorine- or sulfur-containing group in the α, β, or γ position to the carbonyl carbon atom.

4. The process of claim 1, wherein the hydrolase is selected from the group consisting of lipases from bacteria of the *Burkholderia* genera, lipases from bacteria of the *Pseudomonas* genera, and yeasts of the *Candida* genus.

5. The process of claim 4, wherein the lipase is lipase B from *Candida antarctica*.

6. The process of claim 1, wherein n is 0.

7. The process of claim 1, wherein P is a tert-butyl group.

8. The process of claim 1, wherein the reaction with the acylating agent is performed in the presence of the hydrolase in a nonaqueous reaction medium.

9. The process of claim 1, wherein the compound of formula (II) is obtained by
(a) protecting a compound of formula (III)

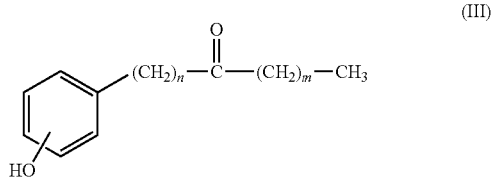

on the OH group to obtain a compound of formula (IV)

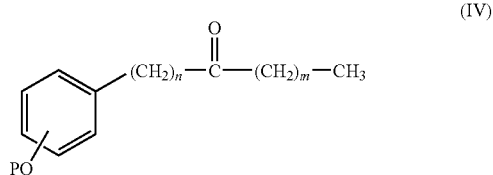

and
(b) subjecting the compound of formula (IV) to a reductive amination to obtain the compound of formula (II).

10. The process of claim 9, wherein the compound of formula (III) is reacted in (a) with isobutene in the presence of an acid.

* * * * *